United States Patent [19]

Nishimura et al.

[11] 4,328,302

[45] May 4, 1982

[54] LITHOGRAPHIC SILVER HALIDE PHOTOGRAPHIC LIGHT-SENSITIVE MATERIAL

[75] Inventors: Tatsuo Nishimura, Ashiya; Hiroyuki Mifune, Ashigara; Yoshiharu Fuseya, Ashigara; Yukihide Urata, Ashigara; Tadao Shishido, Ashigara; Yasuo Kasama, Ashigara, all of Japan

[73] Assignee: Fuji Photo Film Co., Ltd., Kanagawa, Japan

[21] Appl. No.: 232,483

[22] Filed: Feb. 9, 1981

[30] Foreign Application Priority Data

Feb. 8, 1980 [JP] Japan .................................. 55/14625

[51] Int. Cl.³ .............................................. G03C 1/06
[52] U.S. Cl. .................................... 430/264; 430/265; 430/445; 430/446; 430/949; 430/267; 430/611
[58] Field of Search ............... 430/949, 611, 613, 264, 430/265, 267, 302

[56] References Cited

U.S. PATENT DOCUMENTS

| | | | |
|---|---|---|---|
| 3,266,897 | 8/1966 | Kennard et al. | 430/611 |
| 3,397,987 | 8/1968 | Luckey et al. | 430/611 |
| 3,708,803 | 1/1973 | Salesin | 430/949 |
| 4,169,733 | 10/1979 | Iytaka et al. | 430/949 |

FOREIGN PATENT DOCUMENTS

| | | | |
|---|---|---|---|
| 976261 | 11/1964 | United Kingdom | 430/611 |
| 1275701 | 5/1972 | United Kingdom | 430/611 |

*Primary Examiner*—Mary F. Downey

*Attorney, Agent, or Firm*—Sughrue, Mion, Zinn, Macpeak & Seas

[57] ABSTRACT

A lithographic silver halide photographic light-sensitive material is described which scarcely exhibits colored fringe and black pepper, forms halftone dots of good quality whether a fresh or an exhausted developer is used for processing thereof, and which scarcely shows a drop in sensitivity even when a developer contaminated by a fixing solution is used; said material comprises a support and at least one lithographic silver halide emulsion layer, and containing in said emulsion layer or in another hydrophilic colliodal layer which does not contain silver halide emulsion at least one compound represented by formula (I)

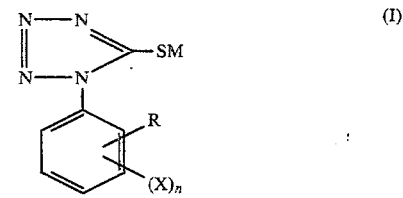

wherein M represents hydrogen, an alkali metal ion or $-NH_4^\oplus$; X represents $-SO_2NHR'$, $-COOM'$, $-SO_3M'$, $-OH$ or $-CONH_2$, wherein M' represents hydrogen, an alkali metal ion or $-NH_4^\oplus$; and R' represents hydrogen or an alkyl group having from 1 to 3 carbon atoms; R represents hydrogen or an alkyl group having from 1 to 3 carbon atoms; and n represents 1 or 2.

17 Claims, No Drawings

LITHOGRAPHIC SILVER HALIDE PHOTOGRAPHIC LIGHT-SENSITIVE MATERIAL

BACKGROUND OF THE INVENTION

The present invention relates to a silver halide photographic light-sensitive material, and more particularly, to a lithographic silver halide photographic light-sensitive material (referred to simply as the "lith sensitive material" hereinafter).

A lith sensitive material comprises a high contrast, silver halide photographic emulsion coated on a support, and can provide a high contrast silver image composed of dots and lines by receiving a development-processing using an extremely high contrast developer such as to have gamma ($\gamma$) of more than 10 (referred to as a lith developer hereinafter), as is described in detail, for example, in J.A.C. Yule, *Journal of the Franklin Institute,* volume 239, page 221 (1945). The thus-obtained, high contrast silver image can be employed as a photomaster for printing.

However, it frequently happens that lith development-processing as described above results in a reddish-brown silver image (referred to as "colored fringe" hereinafter). It is thought that this phenomenon results from the generation of fine colloidal silver particles around silver image and the scattering of light from these particles. These fine colloidal particles are thought to be generated at a stage of development wherein the developed silver has not yet grown to its full size, and therefore has not yet formed a filamentary structure. For instance, the extent of change in color of the silver image, from black to reddish-brown, becomes particularly large when a large amount of polyalkylene oxide compound is incorporated in a lith sensitive material or a lith developer for the purpose of raising image quality, when an exhausted lith developer is used, or when a lith developer is contaminated with even only a small amount of fixing solution. Such colored fringe around silver image is undesirable for a photomaster in which exact reproduction of halftone dot (image area) and line width is required. Therefore, it is strongly desired to prevent colored fringe from occurring.

In general, compounds having thione or mercapto groups, as described, for example, in Japanese Pat. No. 13485/68, C.E.K. Mees and T. H. James, *The Theory of Photographic Process,* 3rd edition, pages 325-328, Mc-Millan, New York (1966), etc., are known to render the color tone of a silver image pure black (referred to as "cool black toning"). Since such compounds were found to exhibit the cool black toning effect in cases that developers of metol-hydroquinone system and developers of phenidone-hydroquinone system were used, it may be analogized that these compounds can be useful for the apparent improvement upon color tone of silver image in developers of other systems also.

As will be described hereinafter, thiones (e.g., 3,4-methyl-thiazoline-2-thione) can undoubtedly impart a cool black tone to a silver image, but suffer the serious disadvantage that they cause a lowering of sharpness in the toe portion of the characteristic curve obtained using a lith developer, and, consequently, cause deterioration of qualities of halftone dots and line images.

On the other hand, mercapto compounds, for example, 1-phenyl-5-mercaptotetrazole and the like, which are well-known in the above-described literatures and so on, can not only impart a cool black tone to the silver image, but can also improve upon the sharpness of the toe portion and thereby, raise the quality of halftone dots. However, they also suffer two serious disadvantages that they increase the frequency of occurrence of black pepper (also known as pepper spots) and cause considerable desensitization when the lith developer used is contaminated by a slight amount of fixing solution by accident.

The term "black pepper" signifies black spots which appear in areas among dots, which areas are normally to be the non-developed part. Such black spots appear in large numbers when the lith developer is close to becoming exhausted, or when the lith developer is contaminated by only a slight amount of fixing solution and thereby, the commodity value as a lith sensitive material is greatly lowered. Further concerning the black pepper, a detailed description thereof appears in H. Zwicky, *Journal of the Photographic Science,* Volume 23, page 159 (1975), and in other papers, but the cause of its occurrence remains unexplained in many respects.

Moreover, it happens that a sharp decrease in the sensitivity is observed in some lith sensitive materials processed using an automatic developing machine. This is, as will be shown hereinafter, supposed to be caused when the lith developer is contaminated by a slight amount of fixing solution through the splash of the fixing solution, a mistake made while working, the passage of processed films (in which a fixing solution remains unremoved in only a trace amount) through the lith developer with the intention of removing pollution from the rack of the developing machine, or so on.

As described above, the compounds reported in the aforementioned art have some effects upon cool black toning, but produce undesirable side effects in the lith development-processing. Some of them spoil the effect of lith development and, therefore, cannot be used in lithographic materials.

SUMMARY OF THE INVENTION

Therefore, a first object of the present invention is to provide a lith sensitive material which can produce silver image having significantly reduced colored fringe, high contrast, and high image quality.

A second object of the present invention is to provide a lith sensitive material which has a high contrast characteristic curve including a sharp toe portion in its characteristic curve, which can, therefore, produce halftone dots of good quality, causes a considerable reduction in black pepper, and causes only a small drop in sensitivity when the developer is contaminated by a fixing solution.

It has been found that the above-described objects are attained by incorporating into a lithographic silver halide emulsion layer or another hydrophilic colloid layer which does not contain silver halide emulsion on a support of a lithographic silver halide light-sensitive material a compound represented by formula (I)

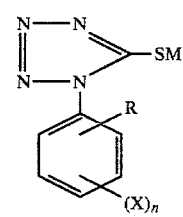

wherein M represents hydrogen, an alkali metal ion (e.g., Na, K, etc.) or —NH$_4^\oplus$; X represents —SO$_2$—NHR', —COOM', —SO$_3$M', —OH or —CONH$_2$ (wherein M' represents hydrogen, an alkali metal ion or —NH$_4^\oplus$, and R' represents hydrogen or an alkyl group containing from 1 to 3 carbon atoms (e.g., methyl, etc.)); R represents hydrogen or an alkyl group containing from 1 to 3 carbon atoms (e.g., methyl, etc.); and n represents 1 or 2.

DETAILED DESCRIPTION OF THE INVENTION

Preferred groups represented by X in the compounds having the above-described formula (I) are —SO$_2$NHR', —COOM' and —SO$_3$M'. More preferable groups for X are groups represented by —SO$_2$NHR'. A particularly preferable group for X is —SO$_2$NH$_2$.

Specific examples of the compounds represented by the general formula (I) are illustrated below:

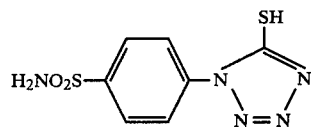
Compound (1)

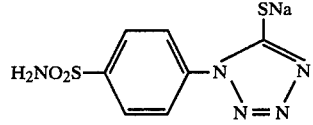
Compound (2)

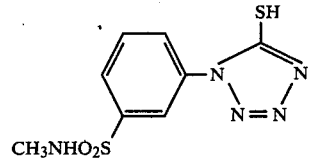
Compound (3)

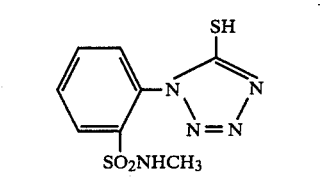
Compound (4)

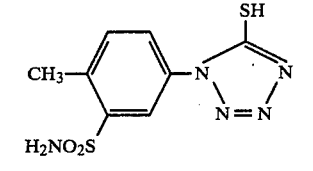
Compound (5)

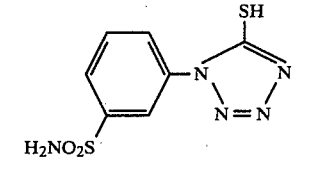
Compound (6)

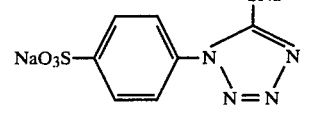
Compound (7)

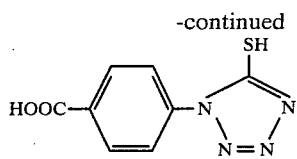
Compound (8)

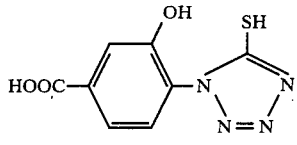
Compound (9)

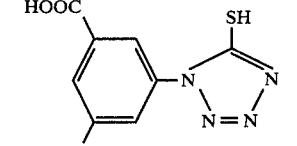
Compound (10)

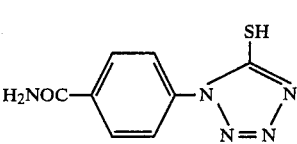
Compound (11)

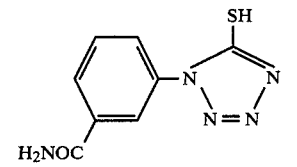
Compound (12)

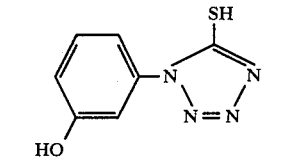
Compound (13)

Compounds according to formula (I) can be prepared by converting

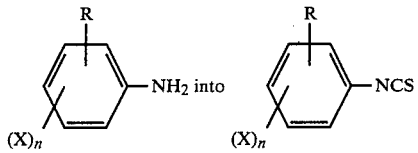

using a known method, for example, through the reaction of an aniline derivative, such as with thiophosgene, and then allowing the resulting phenyl isothiocyanate derivative to react with sodium azide.

Moreover, these compounds can be also prepared by reference to descriptions made in British Pat. No. 1,275,701; U.S. Pat. No. 3,266,897; R. G. Dubenko and V. D. Panchenko, *Khim. Geterotsikl, Soedin., Sb-1; Azots oder zhaschie Geterotsikly*, pages 199–201 (1967); and so on.

SYNTHESIS EXAMPLE

(1) Synthesis of Compound (1)

To 100 ml of water was added 25 g of thiophosgene, and it was stirred thoroughly. Then, 30 g of p-aminobenzenesulfonamide was added with stirring to the resulting solution at room temperature. The stirring of the mixture was allowed to continue for 2 hours, and the crystals precipitated were then separated from the solution by filtration. Thus, 33 g of the crystalline raw isothiocyanate was obtained. mp. 208°–209° C. (decomposed).

The mixture of 33 g of the isothiocyanate, 400 ml of water and 15 g of sodium azide was heated under reflux for 3 hours. The mixture was filtered while hot, and the filtrate was cooled and made acidic with dilute hydrochloric acid. The precipitate formed was removed by filtration, and recrystallized from a methanol-water mixture. Thus, 19.5 g of Compound (1) was obtained. mp. 166°–167° C. (decomposed).

(2) Synthesis of Compound (8)

To 16.5 g of p-amino-ethylbenzoate were added 100 ml of toluene and 16.7 g of N,N-diethyl-thiocarbamyl chloride. The mixture was heated under reflux for 4 hours. After cooling, it was filtered, and the filtrate obtained was evaporated to dryness. The residue was recrystallized from ethyl acetate. To 12.4 g portion of the thus obtained crystals (mp. 53°–54° C.) were added 4.7 g of sodium azide and 50 ml of water. It was heated at 95° C. for 4 hours. After cooling, it was filtered, and the filtrate obtained was made acidic with concentrated hydrochloric acid. The thus precipitated crystals were removed by filtration, and 100 ml of 5% aqueous solution of sodium hydroxide was added thereto. The mixture was heated for 2 hours. After cooling, it was made acidic with concentrated hydrochloric acid. The crystals precipitated were removed by filteration and then recrystallized from methanol. mp. ≧200° C. (decomposed).

The amount of the compound of formula (I) used is generally from $10^{-7}$ to $10^{-2}$ mole, preferably from $10^{-6}$ to $10^{-2}$ mole, and more preferably from $10^{-5}$ to $10^{-3}$ mole, per 1 mole of silver halide contained in the light-sensitive silver halide emulsion layer of the lith sensitive material.

The compound of formula (I) is preferably added to one of the constituent layers of a lith sensitive material; for example, it can be added to a light-sensitive silver halide emulsion layer or to a light-sensitive hydrophilic colloid layer adjacent to the silver halide emulsion layer, such as a surface protecting layer or a subbing layer. The compound can exert its effects upon silver image to some extent even when incorporated in a lith developer, but it can exert its effects to a greater extent when incorporated in the light-sensitive material.

The addition time of the compound is not subject to any particular restriction, but the compound may desirably be added at the time of preparation of a coating solution for a silver halide emulsion layer or another hydrophilic colloid layer. In the case of the addition to a silver halide emulsion, the compound is preferably added during the period between after completion of chemical ripening and before coating.

Next, descriptions of silver halide emulsion layers and other hydrophilic colloid layers which may be employed in the lith sensitive materials of the present invention are described.

Preferred silver halides are silver chlorobromide and silver chloroiodobromide in which each at least 60 mole % (preferably 75 mole % or more) of silver chloride and 0 to 5 mole % of silver iodide are contained. These silver halide grains are not restricted in their forms, crystal habits, size distributions and so on. However, the grain size is preferably 0.7μ or less.

The sensitivity of a silver halide emulsion can be increased without attended by coarsening of the grains using a gold compound such as chloroaurate, gold trichloride, etc.; the salt of a noble metal such as rhodium, iridium, etc.; a sulfur compound capable of producing silver sulfate by the reaction with a silver salt; a reducing substance such as a stannous salt, amines, etc.

In addition, a noble metal salt such as a rhodium salt, an iridium salt or the like, and an iron compound such as hexacyanoferrate (III) or the like can be allowed to be present at the time of the physical ripening or the nucleation of silver halide grains.

After said physical ripening, a combined use of a gold sensitization and a sulfur sensitization is particularly preferred.

As a vehicle for silver halides, gelatin, denatured gelatins, gelatin derivatives or synthetic hydrophilic polymers can be employed.

Into silver halide emulsion layers or other layers, polymer latexes comprising of homopolymers or copolymers which are prepared from alkyl acrylate, alkylmethyacrylate, acrylic acid, glycidylacrylate or/and the like, as described in U.S. Pat. Nos. 3,411,911; 3,411,912; 3,142,568; 3,325,286 and 3,547,650: and Japanese Pat. No. 5331/70, can be incorporated with the intention of raising dimentional stability of photographic materials, improving upon film properties of photographic materials, and so on.

In photographic emulsions, antifogging agents including 4-hydroxy-6-methyl-1,3,3a,7-tetrazaindene, 3-methylbenzothiazole, 1-phenyl-5-mercaptotetrazole and other many heterocyclic compounds; mercury-containing compounds; mercapto compounds; and the antifoggants which are well-known to one skilled in the art, as described in Japanese patent application (OPI) Nos. 81024/74, 6306/75 and 19429/75, and U.S. Pat. No. 3,850,639 can be employed.

The lithographic silver halide emulsions of the present invention can be spectrally sensitized or supersensitized to be rendered orthochromatic or panchromatic by an independent use of cyanine dyes such as cyanine, merocyanine, carbocyanine, etc., or by a combined use of some cyanine dye and other cyanine dye, or some cyanine dye and a different kind of dye such as a styryl dye, etc. In particular, sensitizing dyes described in Japanese patent application (OPI) Nos. 95839/76 and 18311/77, and U.S. Pat. No. 3,567,458 are preferably employed for this purpose.

The lithographic silver halide emulsions of the present invention are not particularly restricted concerning hardening agents to be used therein. Hardening agents which may be used therein include aldehyde series compounds such as formalin, glutaraldehyde and the like, as described in *Research Disclosure*, 17643, chapter X (Dec. 1978), ketone compounds, reactive halogen-containing compounds such as 2-hydroxy-4,6-dichloro-1,3,5-triazine and the like, reactive olefin-containing compounds (e.g., vinylsulfon series compounds), N-methylol compounds, aziridine compounds, carbodiimide compounds and so on.

In photographic emulsions, surface active agents can be incorporated as an auxiliary coating agent for improving upon the photographic property.

Preferred surface active agents which may be used therein include natural surface active agents such as saponin, etc.; nonionic surface active agents of alkylene oxide series, glycidol series and the like; anionic surface active agents containing acid groups such as carboxylic acid group, sulfonic acid group (e.g., surface active agents described in U.S. Pat. No. 3,415,649), phosphoric acid group, sulfuric acid ester group, phosphoric acid ester group, and the like; and amphoteric surface active agents such as amino acids, aminosulfonic acids, sulfuric acid or phosphoric acid esters of aminoalcohols and the like. Particularly preferred surface active agents which may be used therein include a polyalkylene oxide compound.

Polyalkylene oxide compounds employed in the present invention include condensates of polyalkylene oxides, which each is constituted with at least 10 units of alkylene oxides containing 2 to 4 carbon atoms, for example, ethylene oxide, propylene-1,2-oxide, butylene-1,2-oxide and the like (especially ethylene oxide), and compounds having at least one active hydrogen in their respective molecules, such as water, aliphatic alcohols, aromatic alcohols, fatty acids, organic amines, hexitol derivatives and so on; and block copolymers of two or more kinds of polyalkylene oxides. Namely, these polyalkylene oxide compounds are specifically polyalkylene glycols, polyalkylene glycol alkyl ethers, polyalkylene glycol aryl ethers, polyalkylene glycol (alkylaryl) esters, polyalkylene glycol esters, polyalkylene glycol fatty acid amides, polyalkylene glycol amines, polyalkylene glycol block copolymers, polyalkylene glycol grafted polymers and so on.

The number of polyalkylene oxide chain which may be contained in one molecule is not limited to one, but it may be two or more. Where two or more of polyalkylene oxide chains are contained in one molecule, the individual chain may be constituted with not more than 10 alkylene oxide units, but the sum of alkylene oxide units in the molecule must be at least 10. In addition, the individual polyalkylene oxide chain may be constituted with alkylene oxide units different from those of another chain; for instance, one is constituted with ethylene oxide units, and the other is constituted with propylene oxide units. The polyalkylene oxide compound to be employed in the present invention is that which contains preferably 14 to 100 alkylene oxide units.

Specific examples of the polyalkylene oxide compound employed in the present invention are illustrated below:

$$HO(CH_2CH_2O)_9H \tag{1}$$

$$C_{12}H_{25}O(CH_2CH_2O)_{15}H \tag{2}$$

$$C_8H_{17}CH=CHC_8H_{16}O(CH_2CH_2O)_{15}H \tag{3}$$

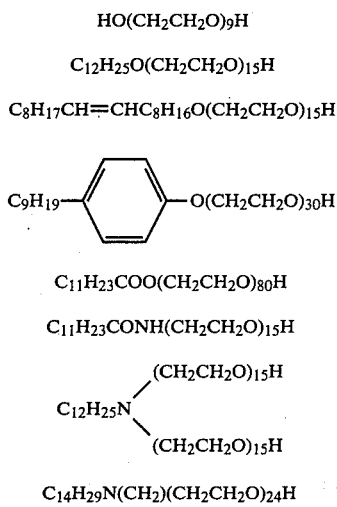
(4)

$$C_{11}H_{23}COO(CH_2CH_2O)_{80}H \tag{5}$$

$$C_{11}H_{23}CONH(CH_2CH_2O)_{15}H \tag{6}$$

$$C_{12}H_{25}N\begin{matrix}(CH_2CH_2O)_{15}H \\ \\ (CH_2CH_2O)_{15}H\end{matrix} \tag{7}$$

$$C_{14}H_{29}N(CH_2)(CH_2CH_2O)_{24}H \tag{8}$$

-continued
$$H(CH_2CH_2O)_a(\underset{\underset{CH_3}{|}}{C}HCH_2O)_b(CH_2CH_2O)_cH \tag{9}$$

$a + b + c = 50$
$b : (a + c) = 10 : 9$

The surface active agents described above may be added to a light-sensitive silver halide emulsion layer or to hydrophilic colloid layers adjacent thereto such as a surface protecting layer, a subbing layer and so on.

The surface protecting layer of the lith sensitive material of the present invention comprises of such a vehicle as described above, for example, gelatin; a surface active agent; a hardening agent; a matting agent; colloidal silica and so on.

As a matting agent, particles of polymethylmethaacrylate or silicon dioxide, which has a size of 0.1 to 10μ, especially 1 to 5μ, are preferably employed.

The lith sensitive material of the present invention further includes a subbing layer, a backing layer and so on as its constituent layers, and it does not have any particular restrictions on materials constituting these layers. Therefore, the materials selected properly from those used in conventional lith sensitive materials can be applied to these layers.

Descriptions in *Research Disclosure*, Volume 176, pages 22-28 (Dec. 1978) provides a guide for preparing silver halide emulsion layers, other layers, a support and so on which the lith sensitive material of the present invention should have.

A lith developer which may be preferably used in the present invention is basically constituted with an ortho- or a para-dihydroxybenzene, an alkali agent, a small amount of free sulfite, a sulfurous ion buffer and so on. The ortho- or the para-dihydroxybenzene which acts as a developing agent can be properly selected from those well-known in the photographic art. Said developing agent which may be used in the present invention is preferably a para-dihydroxybenzene and more preferably a hydroquinone. Specific examples of such a dihydroxy benzene include hydroquinone, chlorohydroquinone, bromohydroquinone, isopropylhydroquinone, toluhydroquinone, methylhydroquinone, 2,3-dichlorohydroquinone, 2,5-dimethylhydroquinone and the like.

Among these hydroquinones, hydroquinone is especially practical. These developing agents may be used independently or in a form of mixture. An addition amount of the developing agent is typically from 1 to 100 g, and preferably from 5 to 80 g, per 1 liter of developing solution. The sulfurous acid ion buffer is used in such an amount as to maintain the sulfite ion concentration in the developing solution at nearly constant, and includes as specific examples aldehyde-alkali hydrogensulfite adducts such as formaldehydesodium hydrogensulfite adduct, etc.; ketone-alkali hydrogensulfite adducts such as acetone-sodium hydrogensulfite adduct, etc.; carbonylbisulfurous acid-amine condensation products such as sodium bis(2-hydroxyethyl)aminomethanesulfonate, etc.; or so on. The sulfurous acid ion buffer is effectively used in an amount of 13 to 130 g per 1 liter of developing solution.

In the developing solution employed in the present invention, free sulfurous acid ion concentration can be controlled by the addition of an alkali metal salt of sulfurous acid, such as sodium sulfite or the like. An addition amount of the sulfite is generally 5 g or less per 1 liter of developing solution. It is preferably 3 g or less.

In many cases, it is preferably for the developer to contain as a development-controlling agent alkali halides (especially bromides such as solium bromide, potassium bromide, etc.). An addition amount thereof is 0.01 to 10 g, preferably 0.1 to 5 g, per liter of developing solution.

In order to adjust the pH value of a developing solution to 9 or higher (and particularly to the range of 0.7 to 11.5), alkali agents are added to the developing solution. For commonly used developing solutions, sodium carbonate or potassium carbonate is used as an alkali agent in a various addition amount. As for many of conventional lith sensitive materials, differences in their photographic capabilities are attributable to a difference in ionic strength of a developing solution used, which difference arises from the difference in the kind of an alkali agent contained therein, the amount of the alkali agent added thereto, or so on. The sensitive material containing the compound of the present invention is little affected by ionic strength of a developing solution used and by the kind of the alkali agent added thereto, and almost the same and that, excellent photographic capabilities can be obtained by the processing with developing solutions differing from one another in alkali agents used and in ionic strengthes thereof. The lith sensitive material of the present invention is advantageous in this respect. However, the lith sensitive material had better be processed with a developing solution having lower ionic strength in order to obtain higher photographic capability.

In addition to the above-described components, the developing solution employed in the present invention can optionally contain water-soluble acids (e.g., acetic acid, boric acid, etc.), alkalis (e.g., sodium hydroxide, etc.) and pH buffers such as salts (e.g., sodium carbonate, etc.). Certain alkalis can not only render the developing solution alkaline but also act as both a pH buffer and a development-controlling agent. Other components which can be further added to the developing solution are a preservative such as diethanol amine, ascorbic acid, kojic acid, etc.; an antifoggant such as benzotriazole, 1-phenyl-5-mercaptotetrazole, etc.; an organic solvent such as triethylene glycol, dimethylformamide, methanol, etc.; and so on.

The developing solution to be prepared in accordance with the above-described embodiment may contain all of the components at the time of use. Before the use, a composition for the developing solution can also be separated into two or more parts and stored independently. For instance, in the case that the developing solution is separated into the component part wherein a developing agent is dissolved and the component part wherein an alkali is contained, these two parts are made usable as the developing solution by the mere dilution and mixing of them at the time of use.

Equally good photographic capabilities can be revealed using either so-called powder type developer and liquid type developer.

In the present invention, a developing temperature ranges preferably from 20° C. to 40° C. However, it is needless to say that development can be carried out at temperatures which are out of the above-described range.

The present invention has a great advantage that nearly consistent sensitivity and good quality of halftone dot can be attained even when the developing temperature is varied within the range of 20° C. to 40° C. The developing time is determined depending on the developing temperature. However, it ranges generally from 10 to 250 sec., and more preferably from 10 to 150 sec.

Development can be carried out by handwork or by using an automatic developing machine. In the case of the processing with an automatic developing machine, there are no particular restrictions as to a conveying technique (e.g., using a roller conveyer, a belt conveyer or the like). Any conveyer type automatic developing machines commonly used in the art can be employed in the present invention. Beyond these, the compositions of processing solutions and the developing process to be adopted here can be determined by reference to descriptions made in U.S. Pat. Nos. 3,025,779; 3,078,024; 3,122,086; 3,149,551; 3,156,173; 3,224,356; 3,573,914; and so on.

In the present invention, exposure for obtaining photographic image may be carried out using general methods. Namely, any of known various light sources, for example, natural light (sunlight), a tungsten lamp, a fluorescent lamp, a mercury lamp, a xenon lamp, an arc lamp, a carbon arc lamp, a xenon flash lamp, a cathode ray tube flying spot and so on, may be used for exposure. An exposure time applicable to the present invention ranges not only from 1/1000 to 1 sec., which is employed in commonly used cameras, but also below 1/1000 sec., specifically from $1/10^4$ to $1/10^6$ sec. which is attainable using a xenon flash lamp and a cathode ray tube, and further beyond 1 sec. The spectral composition of light used for exposure can be optionally controlled by using a color filter. Laser light can also be used for the exposure.

The present invention will now be illustrated in detail by reference to the following examples. However, the invention is not intended to be construed as being limited to these examples.

EXAMPLE 1

A silver halide emulsion which was prepared so as to comprise of 83 mole % of silver chloride, 16.5 mole % of silver bromide and 0.5 mole % of silver iodide was subjected to gold sensitization and sulfur sensitization. The silver halide grains contained therein has an average grain size of about $0.25\mu$.

This emulsion was divided into 16 portions. To each of the portions, 3-ethyl-5-[2-(3-ethyl-2(3H)-thiazolinidene-ethylidene]rhodanine, polyalkylene oxide compound of example-(4), 4-hydroxy-6-methyl-1,3,3a,7-tetrazaindene, sodium dodecylbenzenesulfonate, 2-hydroxy-4,6-dichloro-1,3,5-triazine sodium salt, a dispersion of polyethylacrylate, and the compound of the present invention set forth in Table 1 were added in the order of description, and the resulting emulsion was coated on a polyethylene terephthalate film base.

A negative contact screen (produced by Dainippon Screen Manufacturing Co., 150 L/inch) was superposed on each of these samples in close contact with each other, and it was exposed to light for 10 sec. through a step wedge having a step of 0.1 (log E). After the exposure, each of the samples was developed with two kinds of developers (A) and (B) for 100 sec. at 27° C. using an automatic developing machine and subsequently, fixed (with a fixing solution having the composition described in Table 2), washed and dried. The developer (A) was the fresh lith developer having a composition described in Table 2, and the developer (B) was the exhausted developer of the developer (A) after about 2.5 months' use (which was continued to be replenished so that the sensitivity of fresh developer (A) might be maintained).

The halftone dot quality in the table was evaluated by classifying into 10 grades based on visual judgments regarding the form of halftone dot, sharpness of edge, occurrence of fringe and so on which were passed by observing dots present in each of the parts having blackened areas of 10%, 50% and 90% with respect to each sample by means of a microscope of 100 magnification. The halftone dot quality of grade 10 is the best, and that of grade 1 is the worst. The black pepper was similarly evaluated on visual judgment and classified into 10 grades. Again grade 10 was the best and the grade 1 was the worst (that is, 1 represents the occurrence of a large number of black spots).

As can be seen from Table 1, the processing of the sample 1 with the fresh developer (A) showed indications of the occurrence of fringe, including the consequent reddish-brown coloration of silver image, deterioration of the quality of halftone dots and an occurrence of black spots in a large quantity, and the processing of the sample 1 with the exhausted developer (B) showed to a much greater extent all the indications as described above.

However, in both processings of each of the samples containing their respective compounds of the present invention using the developer (A) and the developer (B), the occurrence of fringe was reduced, the quality of halftone dots was improved, slightly generated fringe was rendered pure black. Thereby, cool toning of silver image was achieved, and further, the occurrence of black spots was prevented markedly.

On the other hand, the samples containing comparison compounds (a) and (b), as illustrated below, which have been described as cool toning agents, exhibited capabilities near to those of the samples of the present invention with regard to the cool toning of silver image (especially of fringe) and the improvements upon the qualities of halftone dots, but they produced black spots in large quantities. Therefore, they were scarcely fit for practical use.

Further, the sample containing the comparison compound (c), as illustrated below, provided silver image which was effectively rendered cool black tone, but had markedly deteriorated quality of halftone dots because of the occurrence of fringe in a large quantity.

Comparison Compound (a)

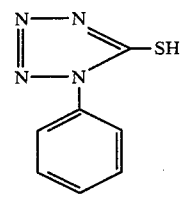

Comparison Compound (b)

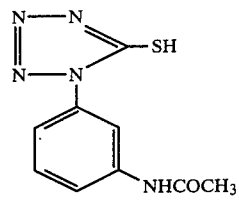

Comparison Compound (c)

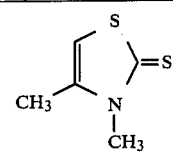

TABLE 1

| Sample No. | Compound | Amount Added mole/mole Ag | Developer (A) | | | Developer (B) | | |
|---|---|---|---|---|---|---|---|---|
| | | | Color of Fringe | Quality of Dots | Black Spots | Color of Fringe | Quality of Dots | Black Spots |
| 1 | None | None | Somewhat Reddish-Brown | 7 | 7 | Reddish-Brown | 5 | 4 |
| 2 | (1) | $2 \times 10^{-5}$ | Cool Black | 8 | 9 | Cool Black | 8 | 8 |
| 3 | (1) | $2 \times 10^{-4}$ | " | 9 | 9 | " | 9 | 9 |
| 4 | (1) | $1 \times 10^{-3}$ | " | 9 | 9 | " | 9 | 9 |
| 5 | (6) | $2 \times 10^{-4}$ | " | 9 | 9 | " | 9 | 9 |
| 6 | (3) | $2 \times 10^{-4}$ | " | 8 | 8 | " | 7 | 8 |
| 7 | (8) | $2 \times 10^{-5}$ | " | 7 | 8 | " | 6 | 5 |
| 8 | (8) | $2 \times 10^{-4}$ | " | 8 | 8 | " | 7 | 6 |
| 9 | (10) | $2 \times 10^{-4}$ | " | 7 | 8 | " | 6 | 6 |
| 10 | (7) | $2 \times 10^{-4}$ | " | 7 | 7 | " | 6 | 6 |
| 11 | (13) | $2 \times 10^{-4}$ | " | 7 | 7 | " | 6 | 5 |
| 12 | (11) | $2 \times 10^{-4}$ | " | 7 | 7 | " | 6 | 5 |
| 101 | (a) | $2 \times 10^{-5}$ | " | 8 | 5 | " | 6 | 3 |
| 102 | (a) | $2 \times 10^{-4}$ | " | 8 | 4 | " | 7 | 1 |
| 103 | (b) | $2 \times 10^{-4}$ | " | 8 | 4 | " | 6 | 3 |
| 104 | (c) | $2 \times 10^{-4}$ | " | 1 | 8 | " | 1 | 8 |

TABLE 2

| Composition of Developer: | |
|---|---|
| Hydroquinone | 15.0g |
| Formaldehyde-sodium Bisulfite Adduct | 50.0g |
| Potassium Carbonate | 30.0g |
| Sodium Sulfite | 2.5g |
| Potassium Bromide | 2.0g |
| Boric Acid | 5.0g |
| Sodium Hydroxide | 3.0g |
| Triethylene Glycol | 40.0g |
| EDTA 2Na | 1.0g |
| Diethanol amine | 15.0g |
| Water | to make 1000 cc |
| Composition of Fixing Solution: | |
| Ammonium Thiosulfate | 150.0g |
| Sodium Thiosulfate | 50.0g |
| Anhydrous Sodium Sulfite | 15.0g |
| Acetic Acid (50%) | 24 ml |
| Sodium Metaborate Tetrahydrate | 12.0g |
| Potassium Alum | 5.0g |

TABLE 2-continued

| | |
|---|---|
| Water | to make 1000 cc |

EXAMPLE 2

Samples 1, 2, 3, 5, 8, 9, 101, 102 and 103, which were prepared in the same manner as in Example 1 above, respectively, were exposed to light through a continuous wedge for 10 sec.

After exposure, each of the samples was development-processed at 27° C. for 100 sec. using different kinds of developers which were prepared by adding the fixing solution used in Example 1 in amounts set forth in Table 3 to the developer (A) used in Example 1 and then, with successive fixed, washed and dried.

The relative sensitivity in Table 3 is expressed as the relative value of the reciprocal of the exposure which is required for obtaining the optical density of 4.0 except for fog density, wherein the sensitivity obtained by the development with the developer (A) is taken as 100 for each of the samples.

TABLE 3

| | Relative Sensitivity | | |
|---|---|---|---|
| Sample No. | Developer (A) as is | 0.2 cc Addition of Fixing Solution to 1 l of Developer (A) | 0.4 cc Addition of Fixing Solution to 1 l of Developer (A) |
| 1 | 100 | 85 | 65 |
| 2 | 100 | 95 | 85 |
| 3 | 100 | 95 | 85 |
| 5 | 100 | 90 | 80 |
| 8 | 100 | 85 | 75 |
| 9 | 100 | 85 | 75 |
| 101 | 100 | 50 | 25 |
| 102 | 100 | 40 | 15 |
| 103 | 100 | 40 | 18 |

As can be seen from Table 3, the drop in the sensitivity which was caused by the contamination of the developing solution with the fixing solution was improved by the addition of the compounds of the present invention. Such an effect was observed especially in samples 2,3 and 5 (wherein the compounds (1) and (6) of the present invention were contained).

On the other hand, a severe drop in the sensitivity was observed in each of comparison samples containing comparison compounds (a), (b) and (c), respectively.

While the invention has been described in detail and with reference to specific embodiment thereof, it will be apparent to one skilled in the art that various changes and modifications can be made therein without departing from the spirit and scope thereof.

What is claimed is:

1. A lithographic silver halide photographic light-sensitive material comprising a support and at least one lithographic silver halide emulsion layer, the silver halides of said at least one silver halide emulsion layer being silver chlorobromide and silver chloroiodobromide in which at least 60 mole % of silver chloride and 0 to 5 mol % of silver iodide are contained, and containing in said emulsion layer or in another hydrophilic colloidal layer which does not contain silver halide at least one compound represented by formula (I)

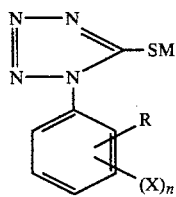

wherein M represents hydrogen, an alkali metal ion or $-NH_4^\oplus$; X represents $-SO_2NR'$, $-COOM'$, $-SO_3M'$, $-OH$ or $-CONH_2$, wherein M' represents hydrogen, an alkali metal ion or $-NH_4^\oplus$; and R' represents hydrogen or an alkyl group having from 1 to 3 carbon atoms; R represents hydrogen or an alkyl group having from 1 to 3 carbon atoms; and n represents 1 to 2.

2. A lithographic silver halide photographic light-sensitive material as in claim 1 wherein X represents $-SO_2NHR'$, $-COOM'$ and $-SO_3M'$.

3. A lithographic silver halide photographic light-sensitive material as in claim 1 wherein X represents $-SO_2NHR'$.

4. A lithographic silver halide photographic light-sensitive material as in claim 1 wherein X represents $-SO_2NH_2$.

5. A lithographic silver halide photographic light-sensitive material as in claim 1, 2, 3, or 4 wherein the compound represented by formula (I) is present in an amount of from $10^{-7}$ to $10^{-2}$ moles per mole of silver halide contained in the light-sensitive silver halide emulsion layer.

6. A lithographic silver halide photographic light-sensitive material as in claim 1, 2, 3, or 4 wherein the compound represented by formula (I) is present in an amount of from $10^{-6}$ to $10^{-2}$ moles per mole of silver halide contained in the light-sensitive silver halide emulsion layer.

7. A lithographic silver halide photographic light-sensitive material as in claim 1, 2, 3, or 4 wherein the compound represented by formula (I) is present in an amount of from $10^{-5}$ to $10^{-3}$ moles per mole of silver halide contained in the light-sensitive halide emulsion layer.

8. A lithographic silver halide photographic light-sensitive material as in claim 1 wherein said silver halides are silver chlorobromide and silver chloroiodobromide in which each 75 mole % or more of silver chloride and 0 to 5 mol % of silver iodide are contained.

9. A lithographic silver halide photographic light-sensitive material as in claim 1 wherein a polyalkylene oxide compound is present in the silver halide emulsion layer or the hydrophilic colloidal layers adjacent thereto.

10. A lithographic silver halide photographic light-sensitive material as in claim 1 wherein a polymer latex is present in the silver halide emulsion layers or other layers.

11. A material as in claim 1, wherein said at least one compound is in said another hydrophilic colloidal layer which does not contain silver halide.

12. A material as in claim 1, wherein X is $-OH$.

13. A material as in claim 1, wherein X is $-CONH_2$.

14. A material as in claim 1, developable to a gamma of more than 10 with a lith developer.

15. A material as in claim 14, wherein said lith developer comprises:

(a) a developing agent substantially comprising an o- or p-dihydroxybenzene alone which is present in an amount of 1 to 100 g/l of developer;

(b) a sulfite present in an amount of 5 g/l or less; and (c) an alkali agent present in an amount that the pH of the developer is 9 or more.

16. A process for forming a high contrast silver image which comprises processing a lithographic silver halide photographic light-sensitive material comprising a support and at least one lithographic silver halide emulsion layer, and containing in said emulsion layer or in another hydrophilic colloidal layer which does not contain silver halide emulsion at least one compound represented by formula (I) with a lith developer

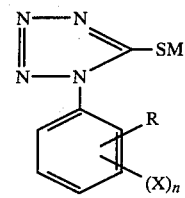

wherein M represents hydrogen, an alkali metal ion or $—NH_4^\oplus$; X represents $—SO_2NHR'$, $—COOM'$, $—SO_3M'$, $—OH$ or $—CONH_2$, wherein M' represents hydrogen, an alkali metal ion or $—NH_4^\oplus$; and R' represents hydrogen or an alkyl group having from 1 to 3 carbon atoms; R represents hydrogen or an alkyl group having from 1 to 3 carbon atoms; and n represents 1 or 2.

17. The process of claim 16, wherein said lith developer comprises:
(a) a developing agent substantially comprising an o- or p-dihydroxybenzene alone which is present in an amount of 1 to 100 g/l of developer;
(b) a sulfite present in an amount of 5 g/l or less; and
(c) an alkali agent present in an amount that the pH of the developer is 9 or more.

* * * * *